(12) United States Patent
Kadomura et al.

(10) Patent No.: US 7,983,383 B2
(45) Date of Patent: Jul. 19, 2011

(54) X-RAY CT APPARATUS

(75) Inventors: Takayuki Kadomura, Tokyo (JP); Taiga Goto, Tokyo (JP); Koichi Hirokawa, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 169 days.

(21) Appl. No.: 12/518,812

(22) PCT Filed: Dec. 12, 2007

(86) PCT No.: PCT/JP2007/073940
§ 371 (c)(1),
(2), (4) Date: Jun. 11, 2009

(87) PCT Pub. No.: WO2008/075595
PCT Pub. Date: Jun. 26, 2008

(65) Prior Publication Data
US 2010/0014628 A1     Jan. 21, 2010

(30) Foreign Application Priority Data

Dec. 20, 2006 (JP) ................................. 2006-342210

(51) Int. Cl.
*G01N 23/00* (2006.01)

(52) U.S. Cl. ............................................. 378/8; 378/16
(58) Field of Classification Search .................. 378/4, 5, 378/8, 16, 97, 108
See application file for complete search history.

(56) References Cited

U.S. PATENT DOCUMENTS

| 2002/0075997 A1* | 6/2002 | Unger et al. ................. 378/98.9 |
| 2002/0085672 A1 | 7/2002 | Ganin et al. |
| 2005/0008115 A1* | 1/2005 | Tsukagoshi ....................... 378/4 |
| 2007/0071172 A1* | 3/2007 | Mollus et al. ................. 378/108 |

FOREIGN PATENT DOCUMENTS

| EP | 1216661 A2 | 6/2002 |
| JP | 4-207675 | 7/1992 |
| WO | WO2005/041775 A1 | 5/2005 |

OTHER PUBLICATIONS

Nov. 10, 2010 European search report in connection with a counterpart European patent application No. 07850491.

* cited by examiner

*Primary Examiner* — Hoon Song
(74) *Attorney, Agent, or Firm* — Cooper & Dunham LLP

(57) ABSTRACT

An X-ray CT apparatus comprising: a scanner unit for rotating one or more X-ray sources for applying X-ray beams having different energy spectra to an object, and detectors disposed opposed to the X-ray sources for detecting transmitted X-ray data on the object, around the object while applying X-rays, reconstructing means for reconstructing a tomogram of the object by acquiring transmitted X-ray data on the object including the two or more different energy spectra by using the scanner, and display means for displaying the reconstructed tomogram; the X-ray CT apparatus further comprising input means for inputting information on an identification tissue of the object to be identified and a separate tissue to be separated from the identification tissue from the tomogram and scanning condition determining means for determining the scanning condition for identifying the identification tissue from the tomogram.
With this, an optimum scanning condition of a multi-energy X-ray CT apparatus can be determined.

20 Claims, 15 Drawing Sheets

FIG.7

| High-kV / Low-kV | 100kV | 110kV | 120kV | 130kV | 140kV | 150kV |
|---|---|---|---|---|---|---|
| 50kV | 93.4% | 96.7% | 98.9% | 99.5% | 99.7% | 99.9% |
| 60kV | 96.6% | 99.1% | 99.9% | 100% | 100% | 100% |
| 70kV | 79.4% | 91.7% | 96.9% | 98.9% | 99.6% | 99.9% |
| 80kV | 31.7% | 56.8% | 77.0% | 88.3% | 93.3% | 96.2% |
| 90kV | 6.6% | 17.9% | 36.9% | 55.1% | 69.6% | 79.5% |
| 100kV |  | 3.9% | 12.4% | 22.9% | 37.8% |  |

FIG.15

| IDENTIFICATION TISSUES | RECONSTRUCTION IMAGE PROCESSING |
|---|---|
| A | DIFFERENCE PROCESS |
| B | ADDING PROCESS |
| C | PROPORTIONAL DISTRIBUTION PROCESS |
| D | DIFFERENCE PROCESS |
| ... | |

US 7,983,383 B2

X-RAY CT APPARATUS

TECHNICAL FIELD

The present invention relates to an X-ray CT apparatus and scan condition determining method thereof, particularly to an optimum scanning condition determining technique for a multi-energy type CT apparatus.

BACKGROUND ART

Multi-energy type X-ray CT apparatuses are for scanning an object to be examined by two or more different energy spectra while rotating one or more X-ray sources and one or more X-ray detectors that are disposed facing each other placing the object therebetween and irradiating X-rays to the object, and generating tomograms (tomographic images) using the X-ray transmission data acquired from the scanning (refer to Patent Document 1 for more details).

In multi-energy type X-ray CT apparatus, by scanning using two or more different energy spectra and calculating difference thereof, etc., an identification tissue that is desired to be identified on the tomographic image and a separate tissue that is in the background of the identification tissue can be displayed with enhanced contrast considering energy dependency of X-ray attenuation characteristics of the tissues thereof, which provides an advantage that the identification tissue can be easily identified (identification ability is higher and the desired identification tissue can be easily found by a radiogram interpreter).

Patent Document 1: JP-A-2004-174253

DISCLOSURE OF THE INVENTION

Problems to be Solved

However, in the conventional technique disclosed in Patent Document 1, a method for determining an optimum scanning condition in the multi-energy type CT apparatus is not taken into consideration.

The objective of the present invention is to provide an X-ray CT apparatus and an scanning condition determination method capable of determining an optimum scanning condition in a multi-energy type X-ray CT apparatus.

Means to Solve the Problem

In accordance with the present invention, an X-ray CT apparatus comprises:

a scanner unit for rotating one or more X-ray sources for irradiating X-rays including a plurality of different energy spectra to an object to be examined, and X-ray detectors disposed facing the X-ray sources for detecting transmitted X-ray data of the object, around the object while irradiating X-rays;

reconstruction means for acquiring transmitted X-ray data of the object including two or more energy spectra by using the scanner unit so as to reconstruct tomographic images of the object; and display means for displaying the reconstructed tomographic images, characterized in further comprising:

input means for inputting information on an identification tissue of the object to be identified and a separate tissue to be separated from the identification tissue on the tomographic image; and scanning condition determining means for determining the scanning condition for identifying the identification tissue from the tomographic image.

Also, an scanning condition determining method of the X-ray CT apparatus is characterized in comprising:

(1) a step for inputting information on an identification tissue of an object to be examined desired to be identified and a separate tissue to be separated from the identification tissue on the tomographic image obtained by the X-ray CT apparatus; and (2) a step for determining the scanning condition for identifying the identification tissue from the tomographic image.

EFFECT OF THE INVENTION

In accordance with the present invention, it is possible to provide an X-ray CT apparatus and scanning condition determining method thereof capable of determining the optimum scanning condition in a multi-energy type X-ray CT apparatus.

BRIEF DESCRIPTION OF THE DIAGRAMS

FIG. 7 shows a table showing identification rates at which the identification tissue is identified the difference image obtained using two tube voltages.

FIG. 15 shows the storing of data regarding processing examples such as difference process, adding process or proportion distribution process, with respect to identification tissues A, B, C, D, . . . .

BEST MODE FOR CARRYING OUT THE INVENTION

A preferred embodiment of the X-ray CT apparatus related to the present invention will be described below referring to the attached diagrams.

Figure 1:
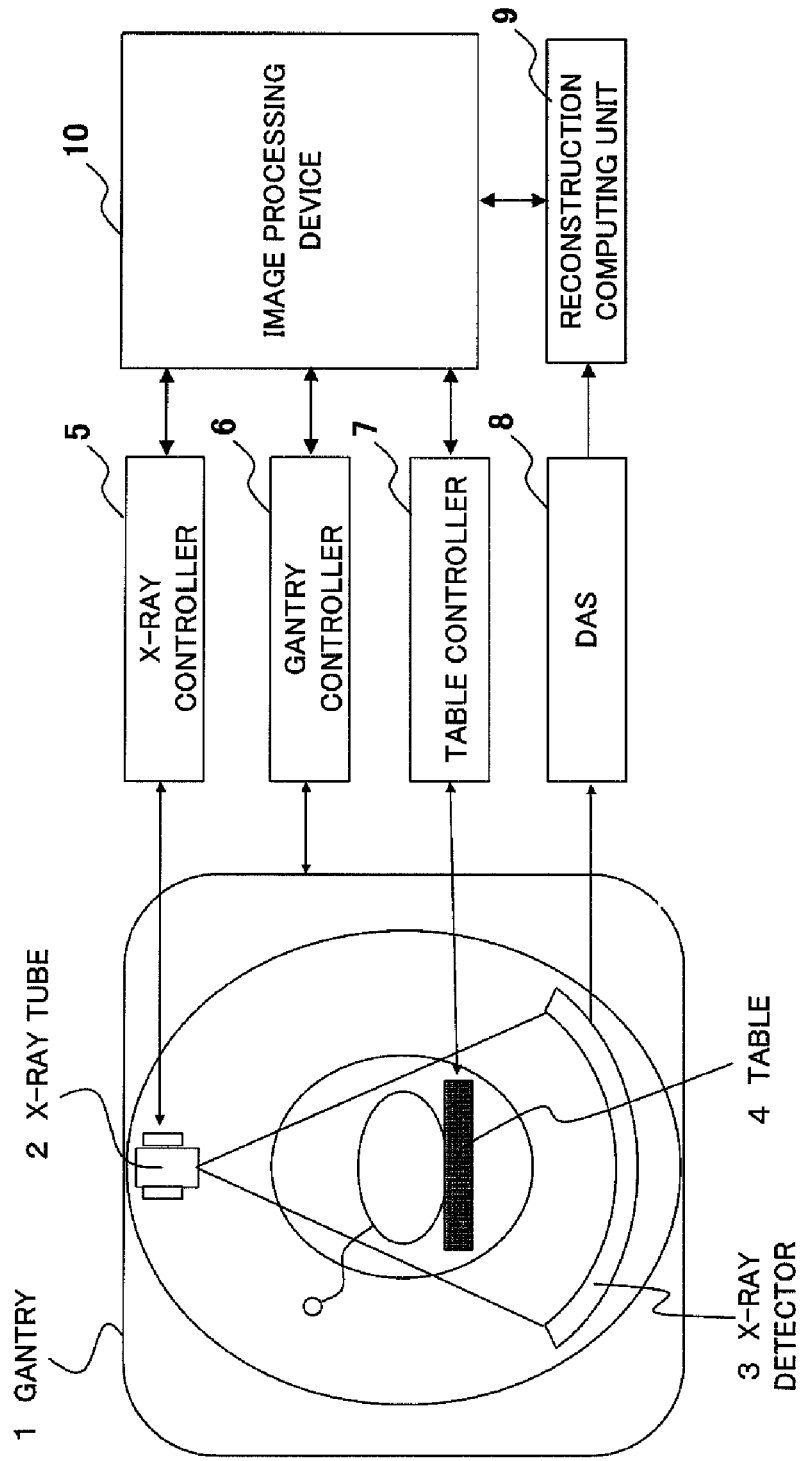
FIG. 1 is a general configuration diagram of a multi-energy type X-ray CT apparatus.

FIG. 1 is a general configuration diagram of a multi-energy type X-ray CT apparatus. The multi-energy type X-ray CT apparatus comprises gantry (scanner) 1, X-ray source 2 mounted in the gantry, X-ray detector 3, table 4, X-ray controller 5 for controlling irradiation of X-rays, gantry controller 6 for controlling the gantry, table controller 7 for controlling the table 4, data analyzing system (DAS) 8 for converting the intensity of incoming X-rays in the X-ray detector 3 into electrical signals, reconstruction computing unit 9 for inputting the electrical signals converted by the DAS 8 and performing reconstruction calculation, and image processing unit 10. The X-ray source 2 irradiates X-rays to the X-ray detector 3 which is placed facing the X-ray detector with object O therebetween, and the X-ray detector 3 detects the X-rays transmitted the object and generates the electrical signals in accordance with the intensity thereof. The X-ray source 2 and the X-ray detector 3 rotate around the object O during one time of scanning.

Operation of the X-ray source 2 and the gantry 1 is controlled by the X-ray controller 5 and the gantry controller 6. The X-ray controller 5 supplies the electrical signals and X-ray generation timing signals to the X-ray source 2, and the gantry controller 6 controls the rotation velocity and position of the components on the gantry 1. The table controller 7 controls the movement velocity and the position of the table 4.

The incoming X-rays in the X-ray detector 3 are converted into digital signals by the DAS 8, and the reconstruction computing unit 9 receives the X-ray data converted into digital signals, carries out image reconstruction and constructs tomograms (image data) of the object O. The reconstructed image data are inputted to the image processing unit 10, and recorded in a data storing device to be described later.

Figure 2:
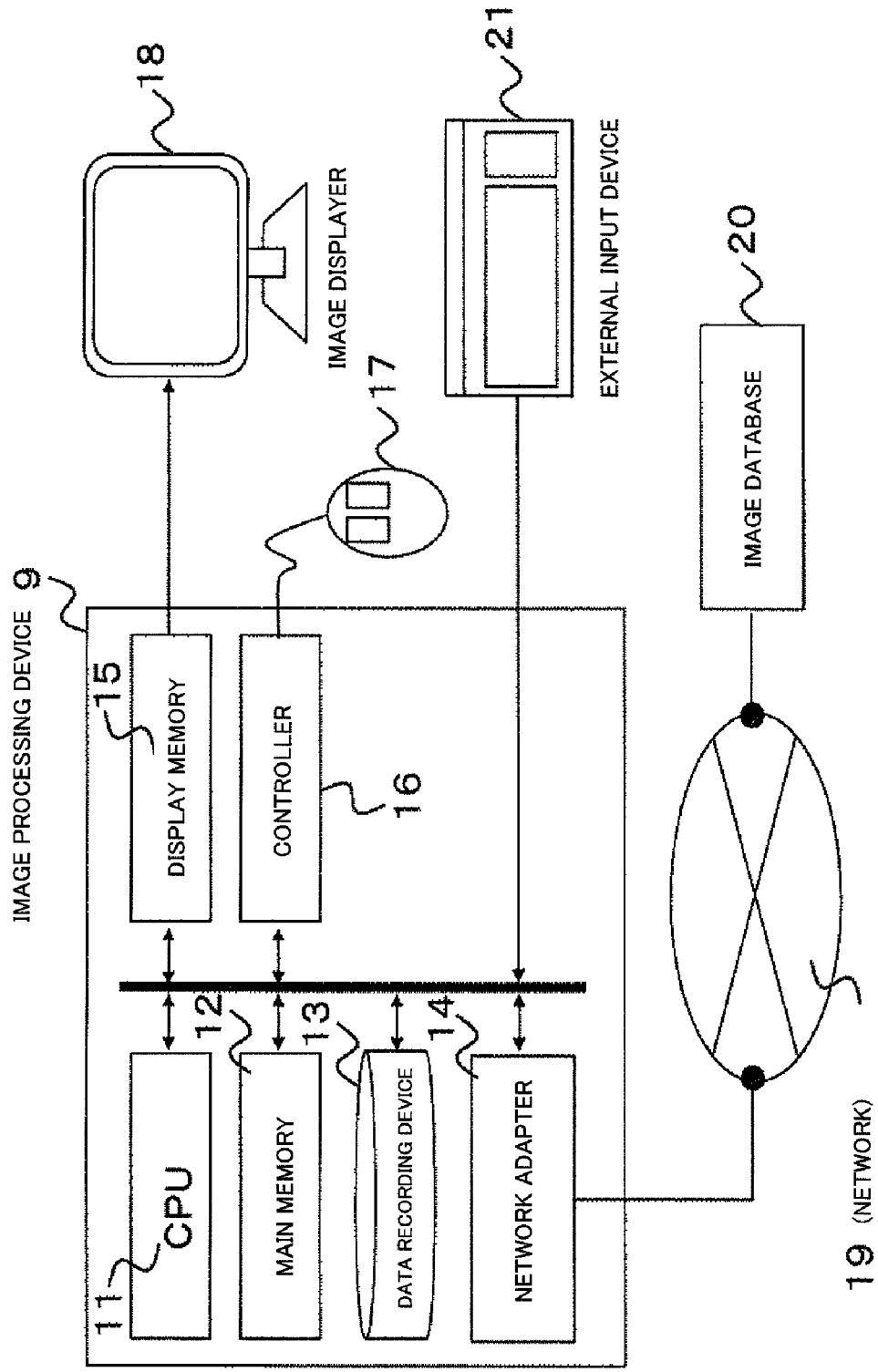
FIG. 2 is a general configuration diagram of an image processing system including image processing device 10.

FIG. 2 is a general configuration diagram of the image processing system including the image processing unit 10. The image processing unit 10 mainly comprises central processing unit (CPU) 11 for controlling operation of the respective components, main memory 12 for storing control program of the image processing unit, data storing unit 13 for storing image data, network adaptor 14 which is a connecting interface to a network, display memory 15 for temporarily storing image data of the object, and controller 16 to be connected to mouse 17.

Also, image display unit 18 for displaying images based on the image data from the display memory 15, mouse 17 (including a pointing device) for operating a software switch on the image display unit, external input unit 21 such as keys for setting the respective parameters or a keyboard comprising switches are further connected to the imaging system. The network adaptor 14 is means for connecting the image processing unit 10 to a network such as a local area network, telephone communication and internet. The data storing unit 13 may be a memory device such as a magnet disk, or a retrievable device for writing in or reading out data with respect to external media. The imaging processing unit 10 is connected to external image database 20 via the network adopter 14 and the network 19, for transmitting/receiving image data among them.

Embodiment 1

Next, embodiment 1 of the present invention will be described.

FIG. 3(a) and FIG. 3(b) are the flowcharts illustrating the process of a step for selecting scanning condition (in concrete terms, combination of two tube voltages) for optimally identifying a desired identification tissue with respect to the separate tissue in a multi-energy scanning and a step for the multi-energy scanning using the previous step, to be performed by the image processing unit configured as described above.

In accordance with means of the flowcharts shown in FIG. 3(a) and FIG. 3(b) (step 1~step 5), the details of the process will be described below.

(Step 1) Specification of Identification Tissue

In the present step, an identification tissue which is a target for identification and a separate tissue which is in the background of the identification tissue is specified.

Figure 4:
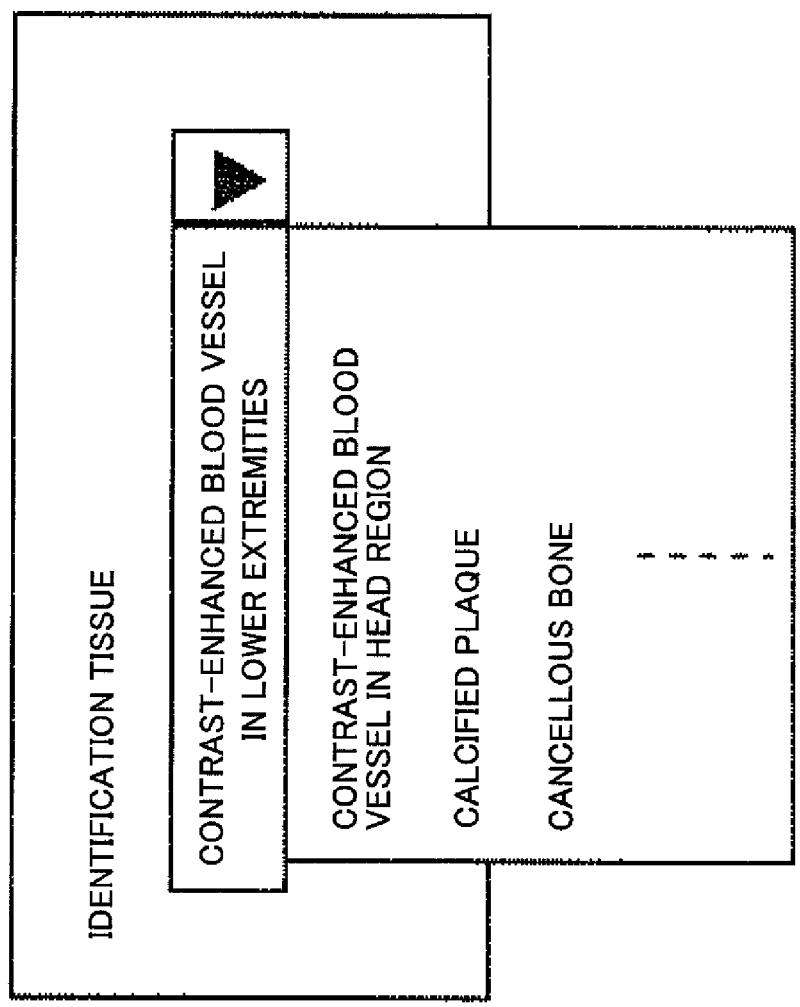
FIG. 4 shows a screen example of image display device 18 by image processing device 9 for specifying an identification tissue.

The identification tissue is specified using a pointing device such as a mouse. FIG. 4 shows a screen example of the image display unit 18 connected to the image processing unit 10 for specifying an identification tissue. On this screen, a selection list from which the desired identification tissue is to be selected (for example, "contrast-enhanced blood vessels in lower limbs", "contrast-enhanced blood vessels in a head-region", "calcified plaque", "cancellous bone", . . . ) is displayed. An operator selects the desired identification tissue upon multi-energy scanning from among the tissues listed in the selection list.

Figure 5:
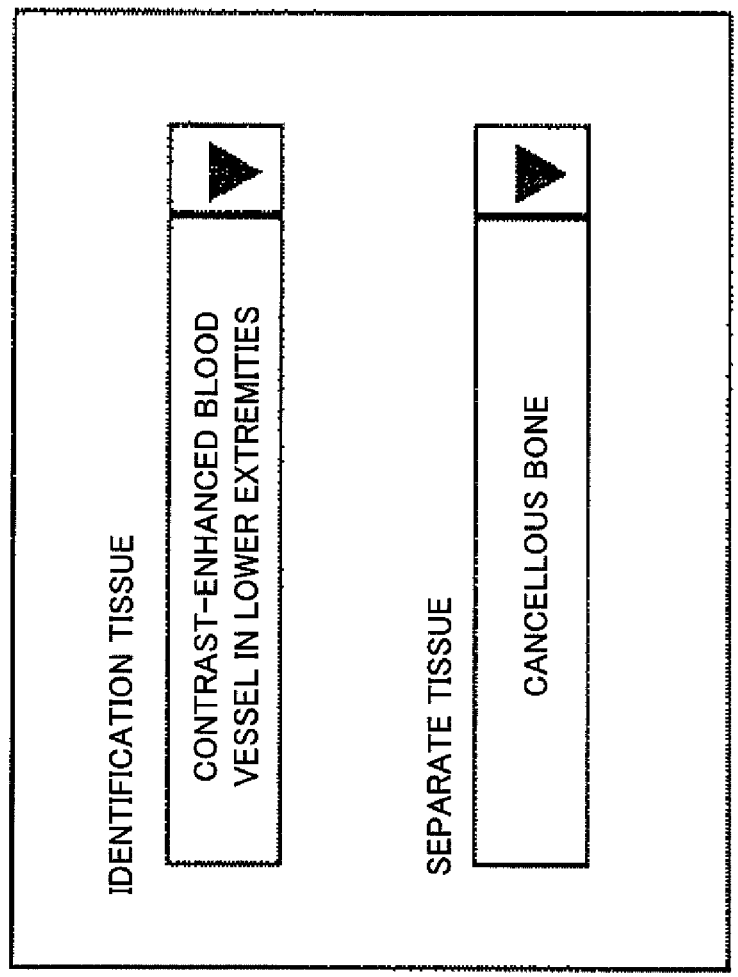
FIG. 5 is a selection list for selecting the identification tissue specified in FIG. 4 and the separate tissue to be separated from the identification tissue.

FIG. 5 shows a selection list from which the identification tissue and the separate tissue specified in FIG. 4 are to be selected. Also in the example in FIG. 5, the separate tissue is to be selected from among the listed chart elements that are "contrast-enhanced blood vessels in lower limbs", "contrast-enhanced blood vessels in a head-region", "calcified plaque", "cancellous bone", etc. In FIG. 5, the "contrast-enhanced blood vessels in lower limbs" is selected as an identification tissue and the "cancellous bone" is selected as a separate tissue as an example. Fat and soft tissue, or white matter and gray matter of a brain, etc. can be listed as the chart elements from which the tissue is to be selected. Identification between gas from contrast agent and inspired air in lungs can also be an example to be listed in the chart.

The screen in the present process for the purpose of specifying a tissue does not have to be limited to the example shown in FIG. 4 and FIG. 5, as long as it displays the list from which an identification tissue and a separate tissue are to be specified.

(Step 2) Selection of Scanning Condition

In the present step, multi-energy scanning condition for optimally identifying an identification tissue set by an identification tissue specifying process, which is in concrete terms the combination of two tube voltages is obtained.

Figure 6:
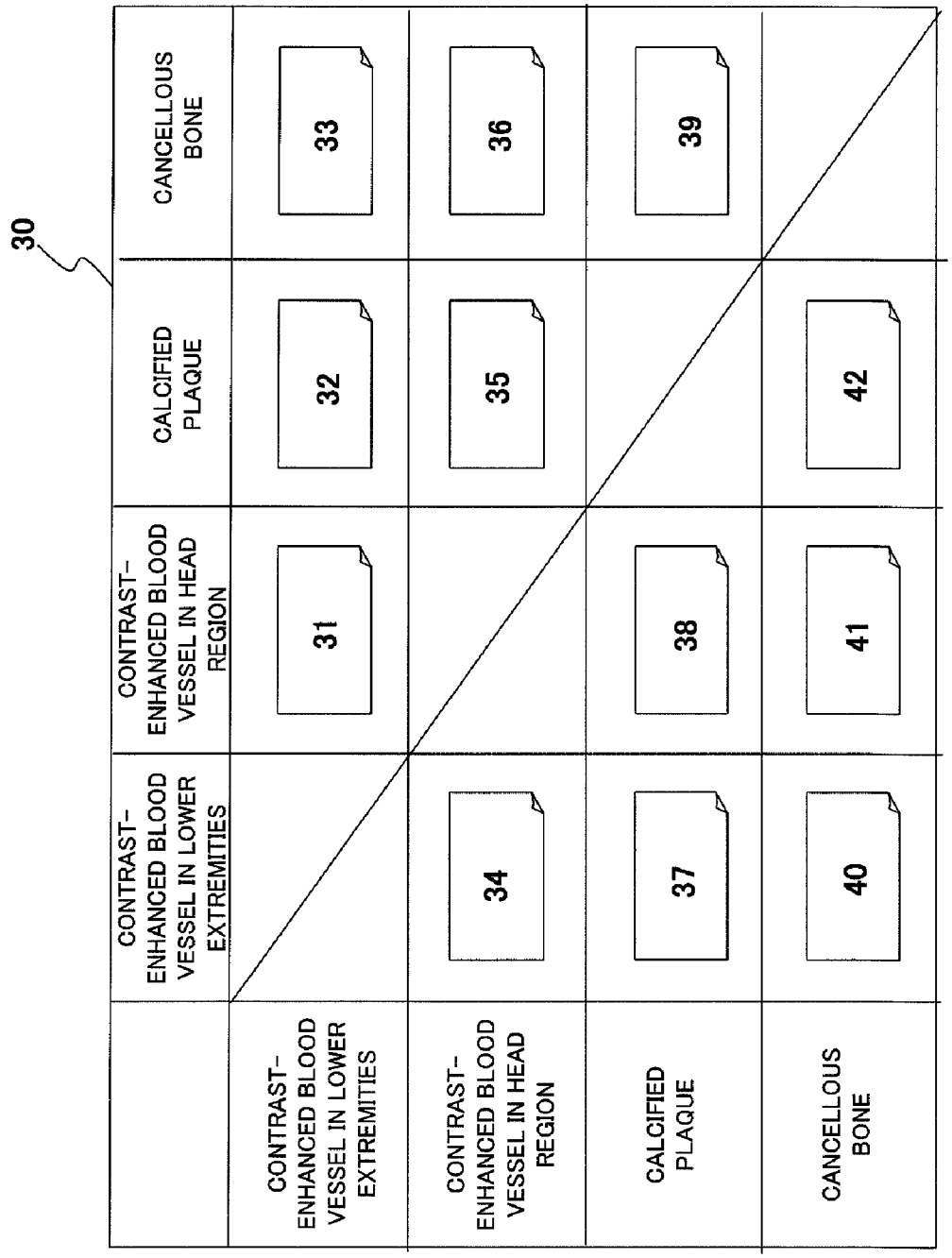
FIG. 6 shows a table showing the tissues.

In a scanning condition calculating process, tissue table 30 shown in FIG. 6 is used. Table 30 shows the identification rates of identification tissues (index regarding the accuracy in identifying identification tissue) on the difference image constructed using the scanning condition (in concrete terms, combination of two tube voltages) for each combination of the tissues previously specified in step 1 (for example in FIG. 6, combination of the identification tissue which is one of the four tissues indicated in FIG. 4 and the separate tissue which is one of the four tissues excluding the tissue selected for the indication tissue indicated in FIG. 4). First, the table of the two tissues (an identification tissue and a separate tissue) specified in step 1 are to be searched from among the table elements 31 ~42. The respective tables look like the one in FIG. 7, which is a display of the identification rates upon identifying the identification tissue from the difference image, etc. between two pieces of images obtained by combining two tube voltages displayed in a table format. The scanning condition having the highest identification rate (more concretely, two different tube voltages) is searched from within the table showing the combinations of the tissues thereof (for example, 31), and the optimal scanning condition (combination of two different tube voltages) is obtained.

The identification rate is to be obtained in advance, defined as an index to indicate the accuracy in identifying an identification tissue, and the higher the value is the more accurately the tissue can be identified. For example, in the case that the identification rate is 90%, it means that the identification tissue can be found on an image with 90% accuracy when the identification tissue is to be identified by performing a multi-energy scanning in the relevant scanning condition (combination of two tube voltages).

An example of the method for calculating the identification rate in the respective scanning condition (combination of two tube voltages) to be used in the present step described below is shown in FIG. 3(b).

(Step 2-1) Calculation of Effective Spectrum of the Irradiated X-ray and X-ray Effective Energy With respect to the respective combinations of a plurality of applicable tube voltages of the X-ray CT apparatus (for example, 50 kV, 60 kV, 70 kV, 80 kV, 90V, 100 kV, etc. on the low energy side and 100 kV, 110 kV, 120 kV, 130 kV, 140 kV, 150 kV on the high energy side), X-rays of the respective tube voltages are irradiated in step 4 and effective spectrum of the irradiated X-rays and the X-ray effective energy that are detected by the X-ray detector are calculated. The effective spectrum of the irradiated X-ray and the X-ray effective energy for each tube voltage may be calculated in advance and stored as database in a data storing device 13.

Figure 8:
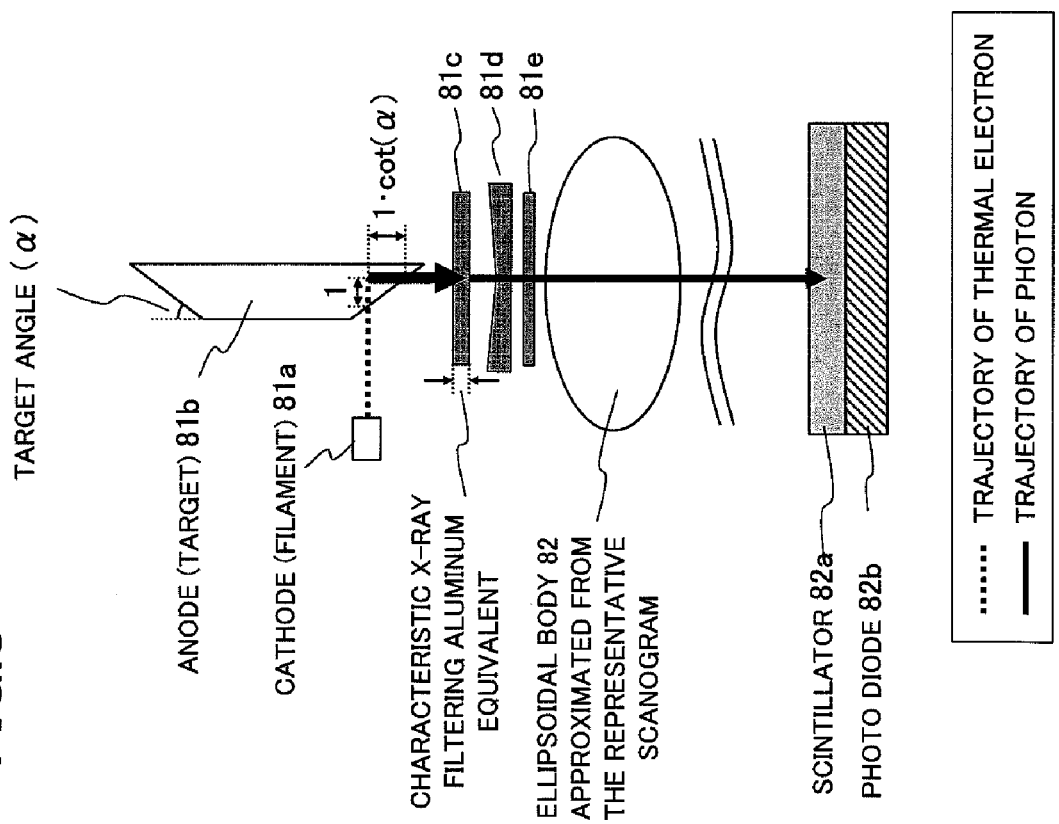
FIG. 8 illustrates effective spectrum and effective energy of an X-ray generated from an X-ray source and detected by X-ray detector 12 which is placed facing the X-ray source, and the attenuation of the X-ray.

FIG. 8 is for explaining the effective spectrum and the effective energy of the X-rays generated from the X-ray source and detected by the X-ray detector 3, and the attenuation thereof. In step 2-1, the spectrum of a bremsstrahlung X-ray is estimated from formula 1 and the spectrum of a characteristic X-ray is estimated from formula 2 based on the intrinsic property of the X-ray CT apparatus itself and the scanning condition for calculating the identification rate, and the spectrum of the irradiated X-ray is estimated by combining them.

$$IE = N\rho/A \int ET_0 (1+T/(m_0 c^2)) Q(dT/dl) - 1 \exp(-\mu(E) lt \cot \alpha) dT \quad (1)$$

$$Ich \propto (T_0/T_{K,L})^{1.63} \quad (2)$$

IE is energy intensity of a bremsstrahlung X-ray having photon energy $E(=h\nu)$, Ich is energy intensity of a characteristic X-ray, N is an Avogadro number, $\rho$ and A are respectively density and atomic weight of the target, m0 is electronmass, c is velocity of light, T0 is energy of an incident electron, Q is energy intensity of the X-ray irradiated from one electron and the value approximately determined by the ratio E/T between photon energy E and electronic energy T, dT/dl is a theoretical formula related to stopping power by Bethe, etc., lt is an incoming distance of an electron, and TK,L is energy necessary for eliminating electrons from K,L electron orbits. As for the calculation of an X-ray spectrum, commonly known other methods may be used.

As shown in FIG. 8, thermal electrons are irradiated from cathode (filament) 81a to anode (target) 81b having target angle α, and the photon produced in the target 81b is generated in the angle approximately vertical to the incident angle of the thermal electron. The photon transmits inherent filtration aluminum equivalent 81c of an X-ray tube, compensating filter (bow-tie filter) 81d and copper filter 81e, and is irradiated to the examination area of the object including the target tissue and the background tissue. The effective spectrum of an X-ray is calculated considering the above-described irradiation path of the X-ray, transmits an X-ray absorber such as ellipsoidal body 82 of water equivalence produced as a pseudo-object from the scanogram scanned at the beginning of the scanning planning, and enters scintillator 82a to be converted into light. The light is detected by photo diode 82b. The ratio of each energy with respect to the entire spectrum is calculated from the calculated effective spectrum of the irradiated X-ray as contribution ratio, and effective energy is calculated based on the calculated contribution ratio.

Figure 9:
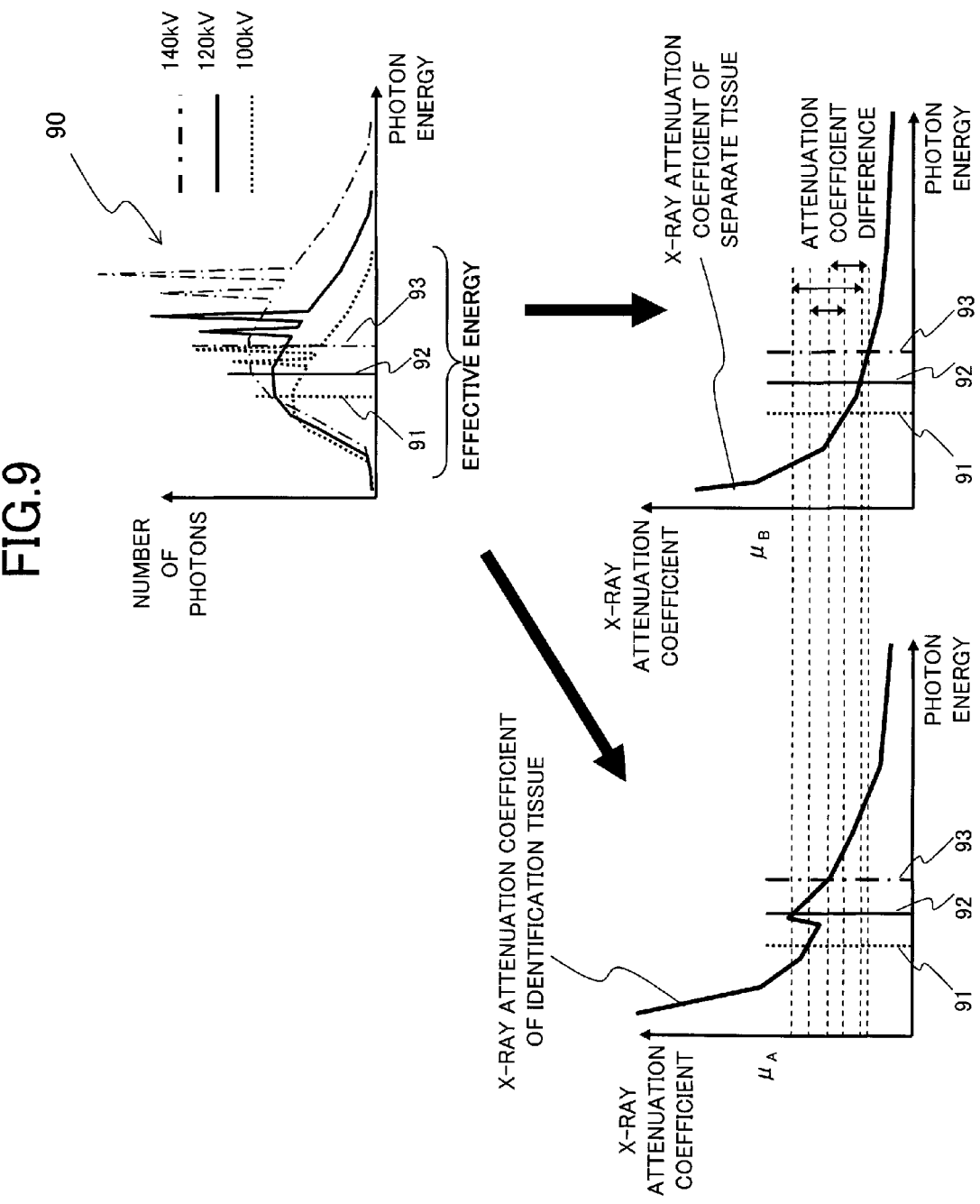
FIG. 9 shows graphs representing distribution of effective spectrum of the irradiated X-ray obtained when tube voltage is 80 kV, 100 kV and 140 kV indicated respectively by a dashed line, solid line and dotted line.

Graph 90 in FIG. 9 displays distribution of the effective spectrum of the irradiated X-ray obtained when the tube voltages are 100 kv, 120 kV and 140 kV, and they are indicated respectively by a dotted line, solid line and dashed line. By performing the commonly known averaging process using distribution of the X-ray effective spectrum of each tube voltage, effective energies 91, 92 and 93 are calculated for the respective tube voltages (equivalent to 100 kv, 120 kV and 140 kV respectively).

(Step 2-2) Calculation of CT Value of Identification Tissue and Separate Tissue

CT values PVA and PVB of the identification tissue (A) in the case that multi-energy scanning is performed in the tube voltages applicable by the X-ray CT apparatus (for example, 50 kV, 60 kV, 70 kV, 80 kV, 90 kV 100 kV, etc. on the lower energy side, and 100 kV, 110 kV, 120 kV, 130 kV, 140 kV and 150 kV on the higher energy side) and the separate tissue (B) corresponding thereto are calculated by formulas 3-1 and 3-2 using attenuation coefficient μA and μB thereof, density of the identification tissue A and the separate tissue B corresponding thereto (DA, DB), attenuation coefficient μW of water under the same condition.

$$PVA = (D_A \mu A - \mu w) \cdot 1000/\mu W \quad (3\text{-}1)$$

$$PVB = (D_B \mu B - \mu w) \cdot 1000/\mu W \quad (3\text{-}2)$$

(Step 2-3) Calculation of Contrast Between Identification Tissue A and Separate Tissue B Contrast "C" (CT value difference) between the identification tissue A and the separate tissue B thereof of the object is calculated using two formulas (3-1) and (3-2) obtained in (step 2-2).

$$C = (D_A \mu A - D_B \mu B) \cdot 1000/\mu w \quad (4)$$

(Step 2-4) Construction of Simulated-Image with Respect to Two Kinds of Tube Voltages In the case that a predetermined tube current value is predetermined, amount of noise on projection data is calculated based on tube current-time product mAs that defines the irradiation amount of the X-rays irradiated from the X-ray source 2. Next, two simulated-images are constructed for the tube voltage on the high-energy side and the tube voltage on the low-energy side, by converting the amount of noise on projection data into the amount of noise on the image data. The simulated-images are constructed such that the identification tissue on the separate tissue has the contrast obtained in step (2-3) and the amount of noise calculated in the present step. When there are two tube voltages, the simulated image is to be constructed respectively.

(Step 2-5) Construction of Difference Images

A difference image between the simulated-image of the low energy condition (Low-kV) and the simulated-image of the high energy condition (High-kV) is constructed.

(Step 2-6) Generation of Histograms

Figure 10:
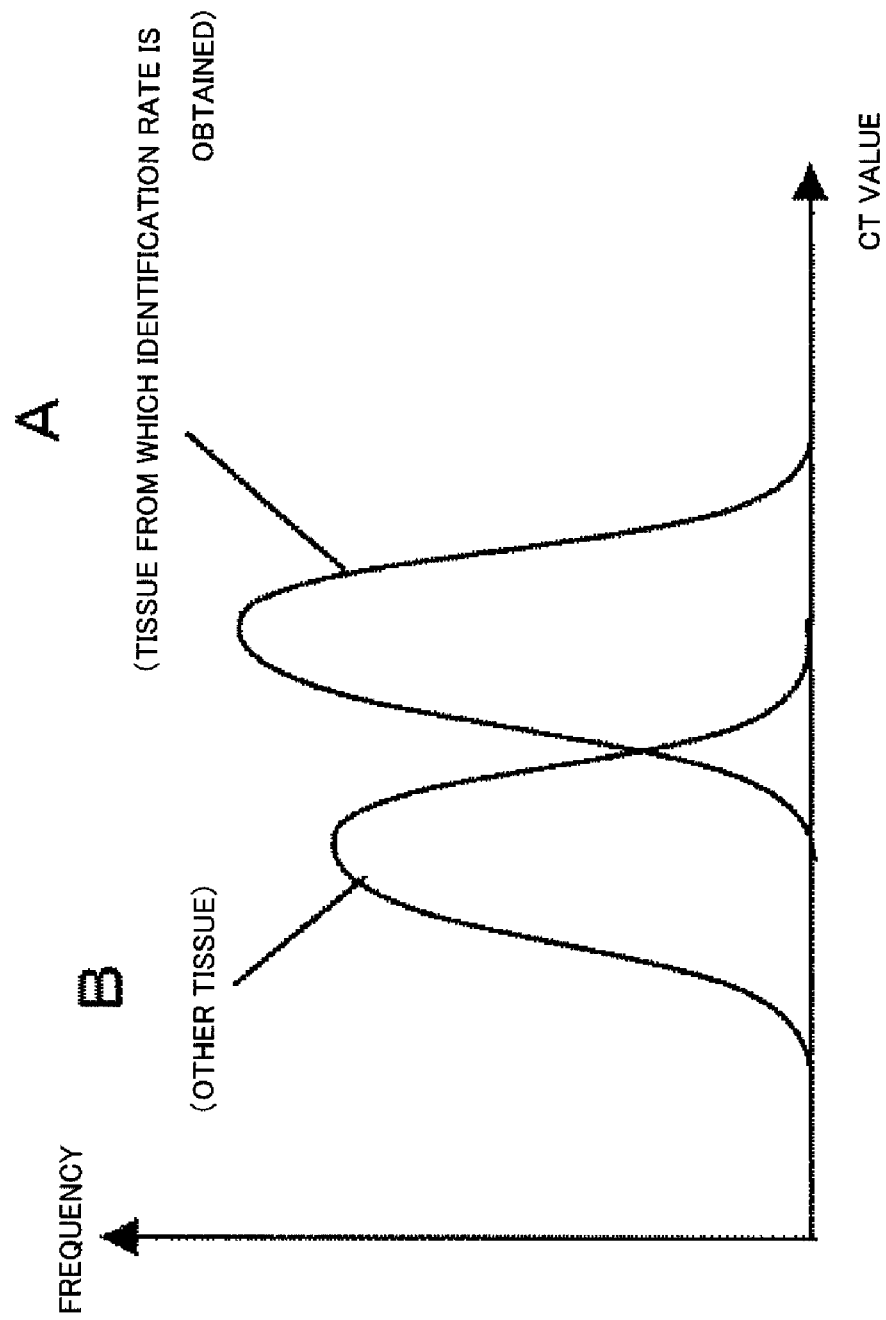
FIG. 10 shows the acquisition of a histogram with respect to each tissue on a constructed difference image.

With respect to each tissue on the constructed difference image, a histogram as shown in FIG. 10 is to be generated. In FIG. 10, the horizontal axis indicates CT values and the vertical axis indicates pixel frequencies. In the diagram, the histogram of identification tissue A for obtaining identification rate and the separate tissue (the tissue desired to be separated with respect to the identification tissue, which are positioned on the background of the identification tissue) B is illustrated. The histogram is to be obtained with respect to the combinations between the respective tissues, for example, the four tissues shown in FIG. 6.

(Step 2-7) Derivation of Threshold CT Value

Figure 11:
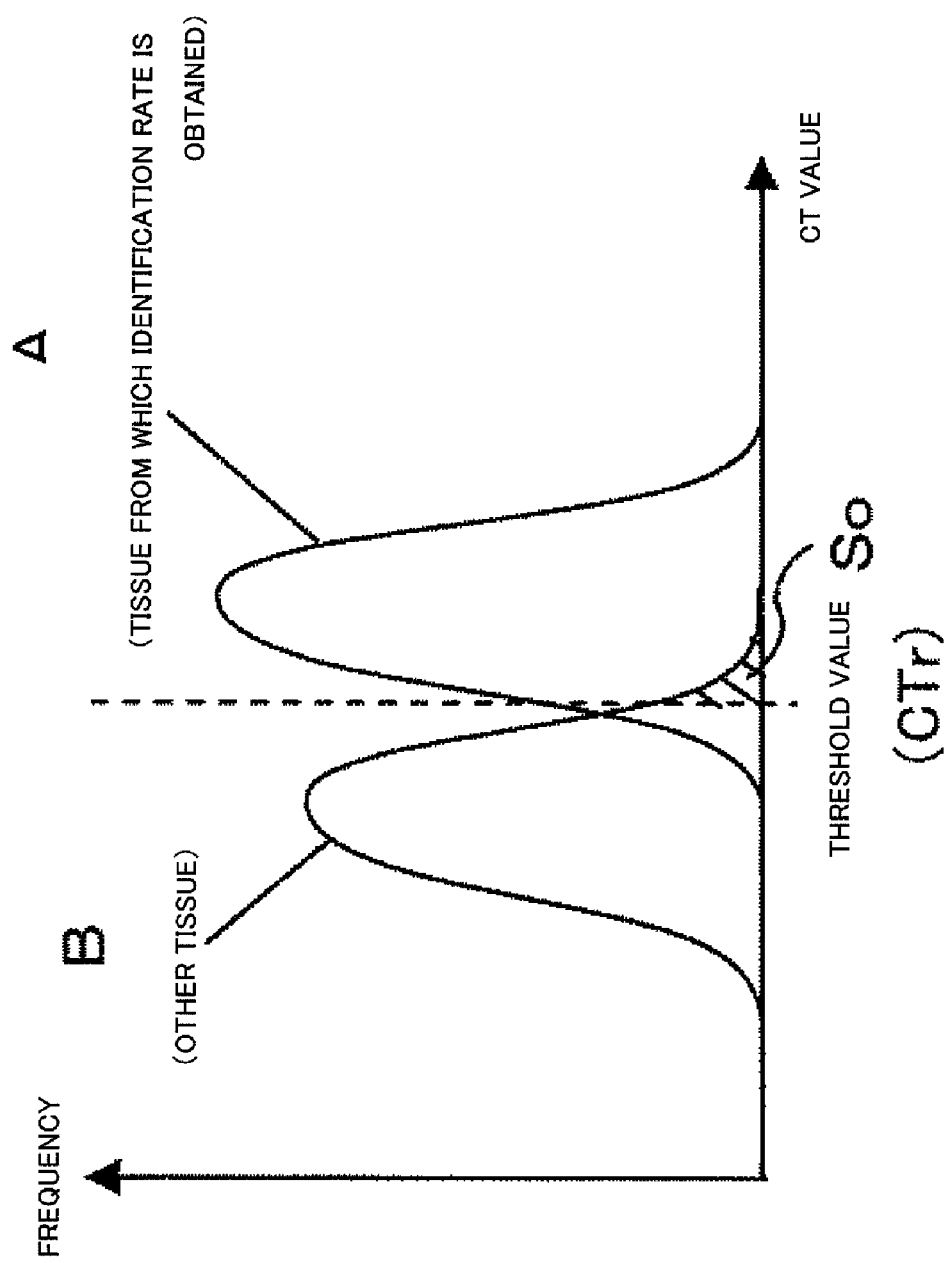
FIG. 11 illustrates acquisition of a threshold value on a histogram so that the ratio on overlap of the component of the tissues other than the identification tissue for obtaining identification ability (separate tissue) and distribution of identification tissues turns out to be below a predetermined ratio.

As shown in FIG. 11, the threshold value wherein the ratio of the components of the tissues other than the identification tissue for obtaining identification ability (separate tissue) overlaps with the distribution of the identification tissue becomes less than a predetermined ratio is to be obtained by the histograms. This is for obtaining the CT value to be area "S0" (less than a certain ratio) which is indicated by the shaded portion in FIG. 11, as threshold value CTr.

Figure 12:
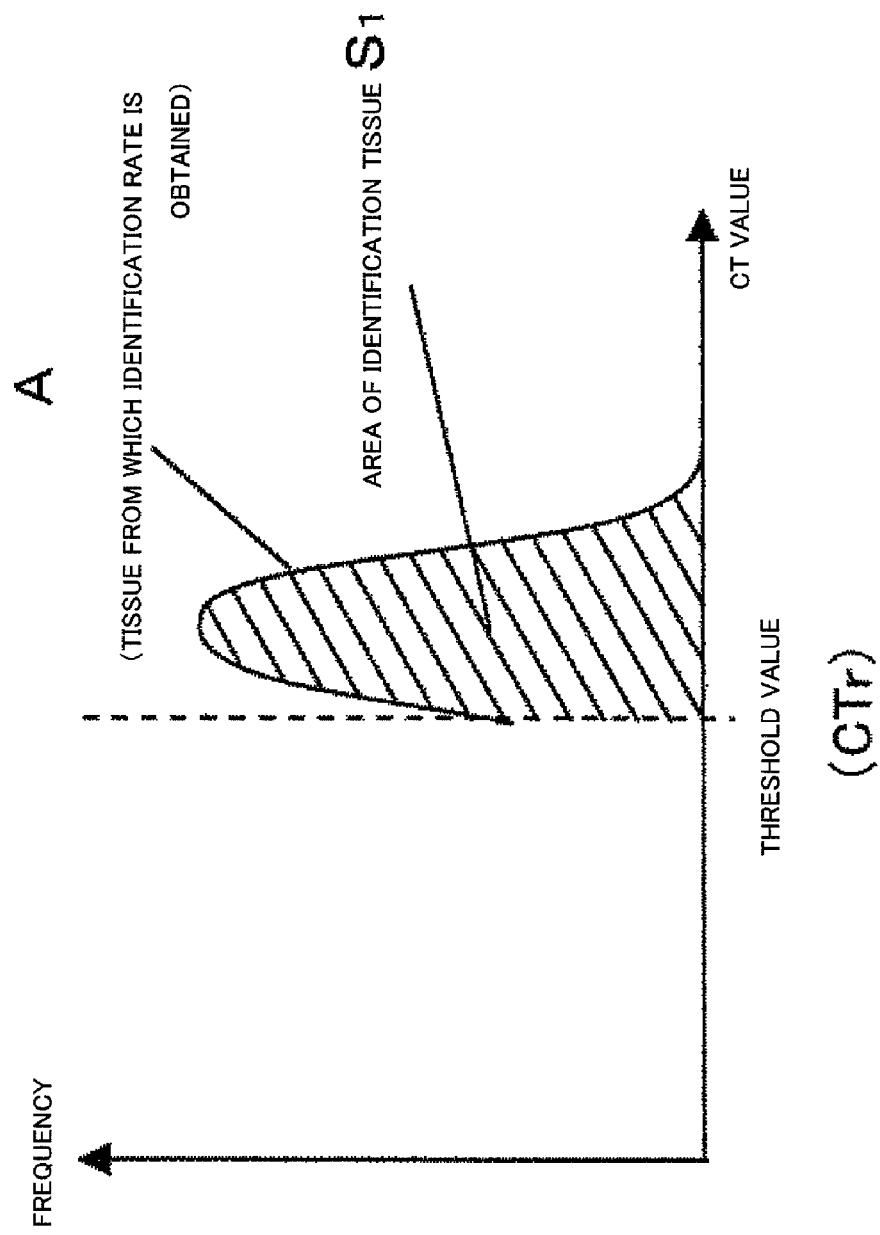
FIG. 12 illustrates acquisition of area S1 (pixel number) of the identification tissue having the CT value which is more (or less) than a threshold value.

(Step 2-8) Derivation of Area of Identification Tissue Having CT Value More than a Threshold As shown in FIG. 12, area S1 (pixel number) of the identification tissue having the CT value which is more than (or less than) a threshold value is to be obtained. This is for obtaining area S1 of identification tissue A having the CT values which are more than the threshold value CTr selected in FIG. 8 (in other words, the remained CT values from which the CT value that are less than CTr are eliminated).

(Step 2-9) Derivation of Total Area of Identification Tissue

Figure 13:
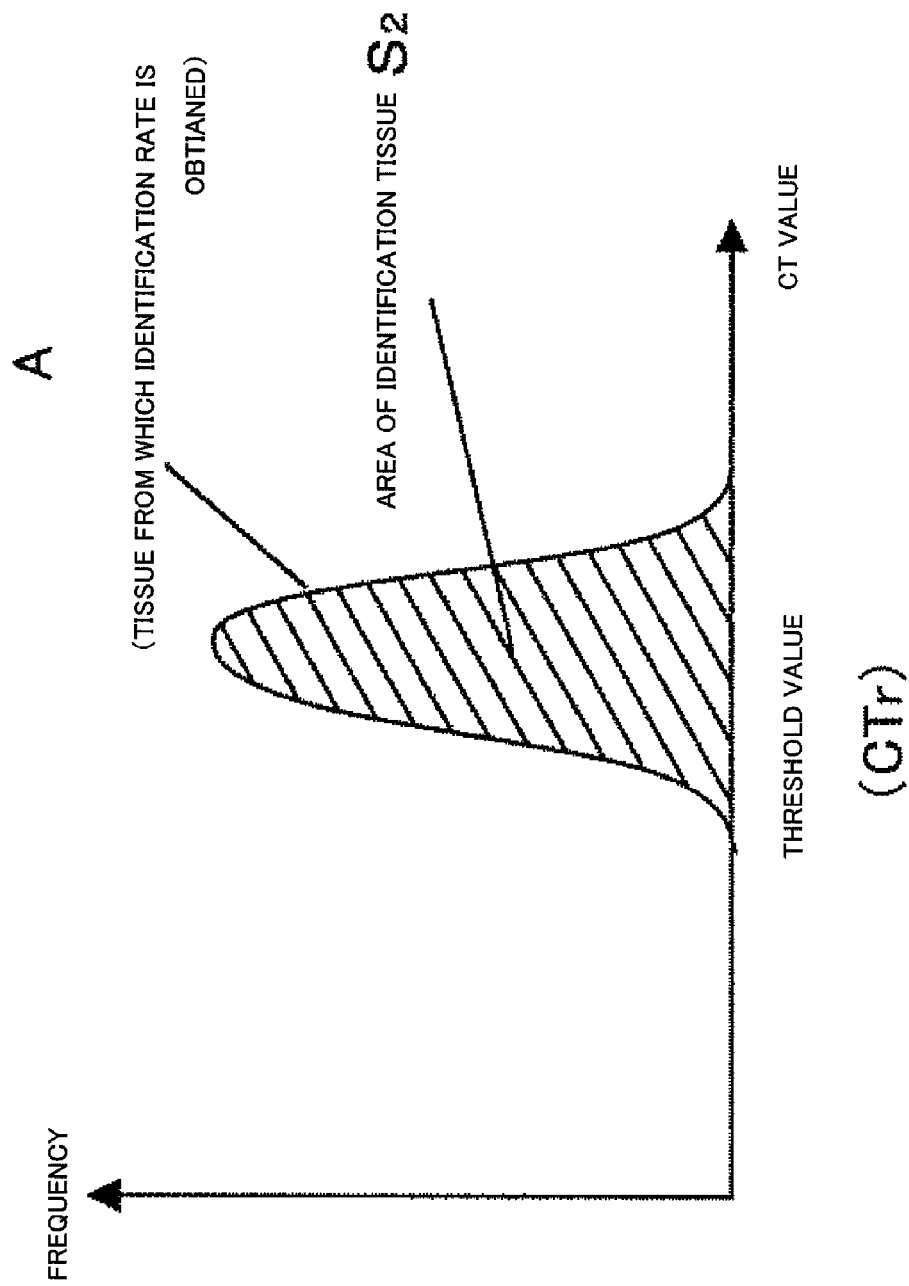
FIG. 13 illustrates acquisition of total area S2 (pixel number) of identification tissue.

As shown in FIG. 13, total area S2 (pixel number) of the identification tissue is to be obtained.

This is for obtaining area S2 of the tissue A before eliminating the CT values using the threshold CTr.

(Step 2-10) Derivation of Identification Rate K

The ratio S1/S2 between the area S1 of the identification tissue A having the CT value more than the threshold value and the total area S2 of the identification tissue is set as identification rate K. The calculation method does not have to be limited to the above-mentioned example, and any method for calculating the ratio for identifying the tissue may be used.

Figure 14:
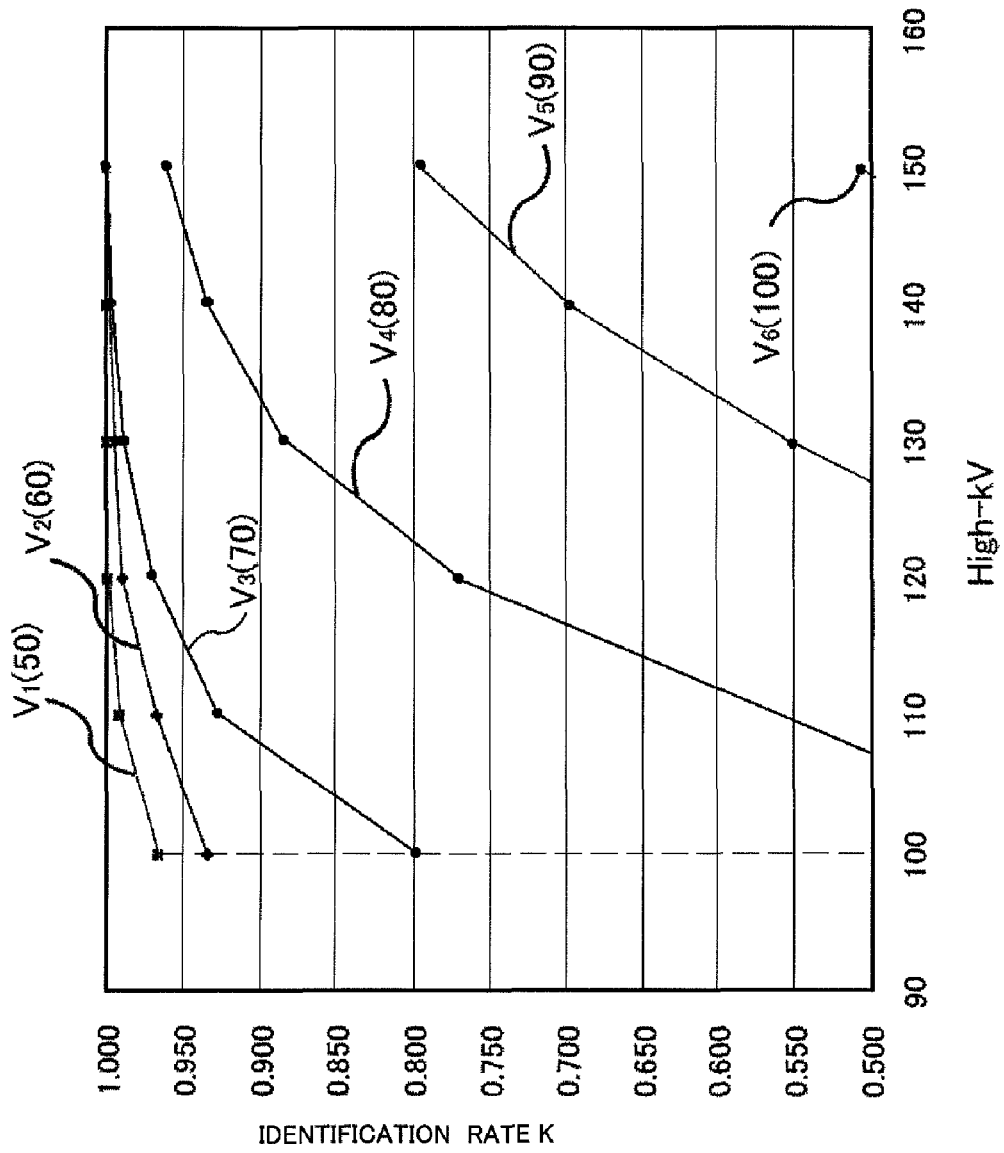
FIG. 14 shows a graph of the identification rate obtained in each combination of high-energy condition (High-kV) and low-energy condition (Low-kV).

The identification rate is to be obtained for each combination of high energy condition (High-kV) and low energy condition (Low-kV) in accordance with the above-described calculation method. FIG. 14 is a graph of the identification rate obtained by the above-described calculation method.

FIG. 14 is a concrete example with respect to an identification tissue A (for example, "contrast-enhanced vessels of lower limbs"), and an example that the voltage value of high energy (High-kV) (90 kV~160 kV) is indicated by the horizontal axis, identification rate K is indicated by the vertical axis, and low energy V1~V6 (50, 0, 70, 80, 90, 100 kV) is adopted as parameters. From the graph, it can be recognized among the low energy side of the tube voltages, that the identification rate K is high in the energy that is lower side (50~70 kV), and the identification rate decreases in the energy that is higher side (80 kV~100 kV). Also among the tube voltages on the high energy side, it can be recognized that the identification rate is approximately low in the energy that is lower side (100, 100 kV).

The graph such as the one shown in FIG. 14 is to be obtained for every combination of the identification tissues and the separate tissue. Then the obtained ratios are recorded in a table as data. FIG. 7 is an example of a table showing the data in FIG. 14 as a memory.

In step 2, along with determination of scanning condition, acquisition of image processing mode for identification is also performed. Image processing mode for identification is for the purpose of identifying an identification tissue from the high energy image and the low energy image obtained by the above-calculated scanning condition. At this time, the image processing performed at the time of obtaining the identification rate is recorded in advance, and the processing is performed between the high energy image and the low energy image using the recorded imaging process so as to acquire an image by which the identification tissue can be presented clearly.

An example of the forementioned stored data is shown in FIG. 15. With respect to identification tissues A, B, C, D, . . . , processing examples such as difference process, adding process or proportional distribution process are stored as data.

Also, the method for calculating the identification rate by searching similar images from the past each time or the calculating method using the pseudo-image constructed by a computer can be used instead of keeping identification rates as a table chart as described above.

Here, extraction of the optimal identification condition will be described.

In the examples of FIG. 14 or FIG. 7, the combinations of high energy and low energy of which the highest value of identification rate is 100% are as below.

(H)130 kV-(L)60 kV, (H) 140 kV-(L)60 kV, (H)150 kV-(L) 60 kV

There is a method to select one combination from among the above-mentioned combinations as the optimal identification condition.

On the other hand, there is a method to select one combination from among the combinations having more than 90%, but not 100%, of identification rate. There are 16 cases of such combinations in FIG. 7, and by setting the voltage of high energy, for example, as 120 kV, and the tube voltage which makes the combination having the highest identification rate between the 120 kV of high energy is selected from among the tube voltages on the low energy side.

In the example of FIG. 7, 60 kV on the low energy side is to be selected to make the combination between 120 kV of high energy side in order to have the highest identification rate. On the contrary, by fixing the voltage on the low energy as 70 kV, the voltage of the optimal high energy can be selected. In the example of FIG. 7, 150 kV is to be selected.

Also, if an operator determines that the identification rate in the range of 50%, not the high identification rate, is sufficient for tissue identification, there are cases that the combination such as (H)130 kV-(L)90 kV is to be selected.

As for the cases such as voltage is restricted, X-ray irradiation amount needs to be saved or electric power consumption is limited, there are cases that an operator selects the optimal voltage combination under such various restrict-ions.

Further, there is a case that more than two identification tissues are desired to be identified on one image. In such case, by using a value such as an average value of the respective identification rates of more than two identification tissues, it can be set so that the combinations of voltages to make the value high are to be selected.

As described above, in the case of selecting optimal tube voltage, the combination having the high identification rate may be selected or the selection may be performed considering other factors (for example, the voltage on the high energy side needs to be a fixed value in advance, the voltage on the lower energy side needs to be a fixed value in advance, or an operator decides that the degree of identification rate necessary for identifying the identification tissue).

(Step 3) Presentation of Scanning Condition

In the present step, the scanning condition for identifying a tissue obtained from the table 30 using the scanning condition calculating process and the identification rate of the condition thereof are displayed.

(Step 4) Multi-Energy Scanning

In the present step, the transmission data of the same object imaged by more than two different energy spectra upon multi-energy scanning is obtained by the scanning condition acquired in step 2. There are various methods in multi-energy scanning that are commonly known such as the method wherein the apparatus has two X-ray sources and X-ray detectors for acquiring transmission data having two different energy spectra by adding different tube voltages from the respective X-ray sources, and the method which adds a filter in front of the X-ray source so as to generate different energies caused by the difference depending on having or not having the filter.

As for the method for multi-energy scanning to be used in the present invention, any method may be used as long as it acquires the transmission data of the object having more than two different energy spectra.

(Step 5) Construction of Tissue Identification Image

In the present step, the image for optimally identifying the tissue that is specified using transmission data of the object having more than two different energy spectra acquired in the multi-energy scanning is constructed. Since the image for optimally identifying the specified tissue is used for calculating identification rate in the scanning condition calculation process, the image processing for constructing the image there of is to be used here.

While the image processing is explained above using FIG. 15, there are various image processing methods other than the difference processing illustrated as an example of the identification rate calculation in the above-described scanning condition calculating process, such as averaging process of a High-kV image and Low-kV image, weighted difference or averaging process and Compton/photoelectric degradative process.

While a voltage is indicated above as scanning condition, there are cases to add a current instead. There are also cases to specify a slice width.

Figure 3:
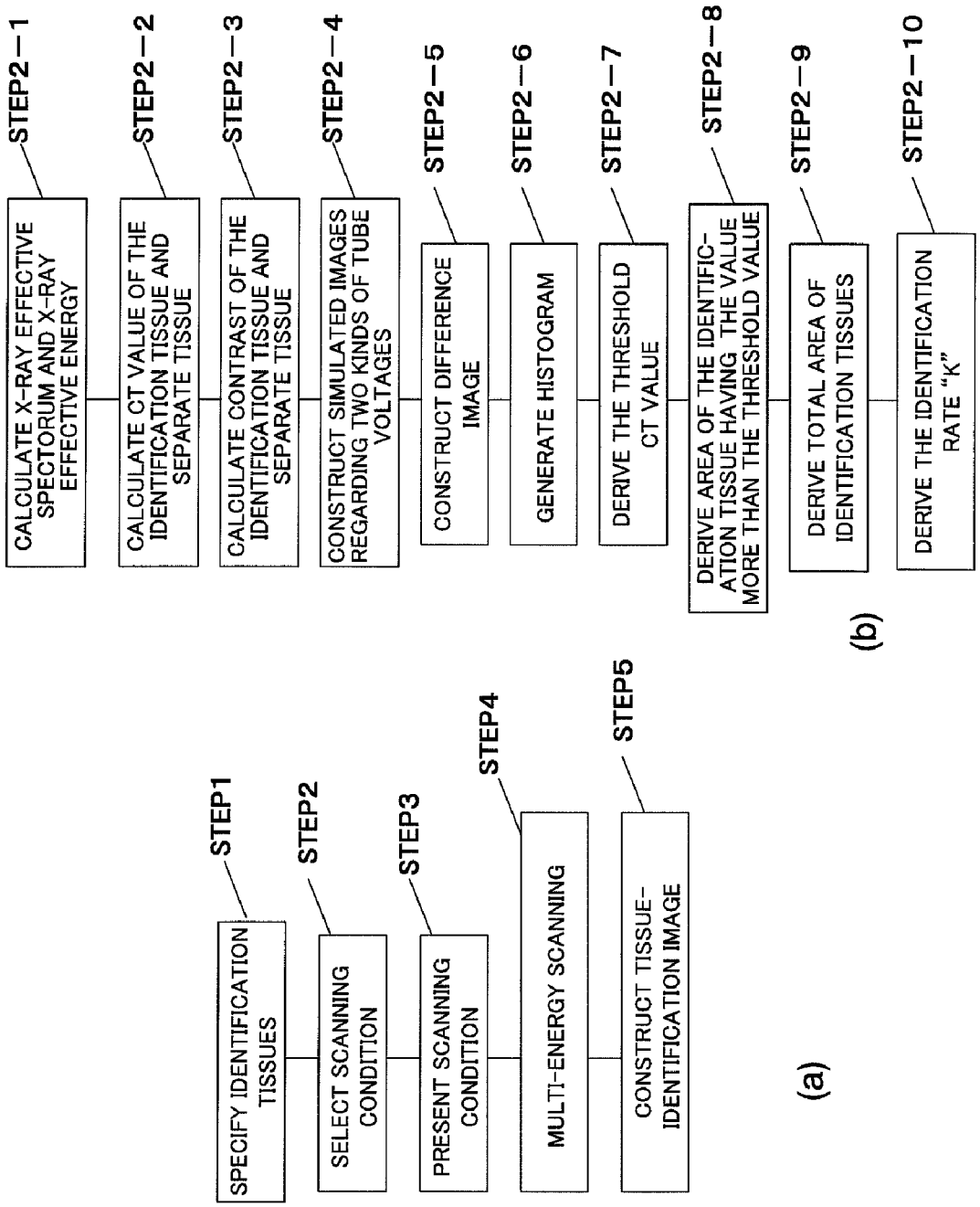
FIG. 3 is a flowchart of an example illustrating the process of a step for determining the scanning condition (in concrete terms, combination of two tube voltages) for optimally identifying desired identification tissues by an operator with respect to separate tissues in multi-energy scanning and a step of multi-energy scanning using the determined scanning condition.

The X-ray CT apparatus related to the embodiment of the present invention comprises the program for implementing the flow chart shown in FIG. 3(*b*) to perform step 2 in FIG. 3(*a*), as scanning condition setting means for determining scanning condition for identifying an identification tissue from a tomographic image obtained by an X-ray CT apparatus. The scanning condition setting means comprised as a program, etc. may be spectrum selecting means of the irradiated X-ray for selecting more than two energy spectra from among the plurality of different energy spectra, and the irradiated X-ray spectrum selecting means may be set for selecting the voltages of the plurality of different energy spectra.

In concrete terms, the scanning condition determining means may comprise calculation means for calculating the index related to accuracy in identifying the identification tissue on a tomographic image which is reconstructed using transmitted X-ray data generated by more than two energy spectra that are arbitrarily selected. Also, the calculation means may be set so as to calculate the index in relation to the combination of the plurality of tube voltages of the plurality of different energy spectra.

Also, the irradiated X-ray spectrum selecting means may be set so as to select the combination of the tube voltages having the index with high accuracy from among the indexes. Also, the display means may be set so as to display the above-described indexes in the form of a table chart with respect to the combinations of the plurality of tube voltages.

Also, the scanning condition determining means may comprise:

storing means for storing a plurality of different energy spectra and X-ray attenuation coefficient of a number of tissues of the object; and tissue selecting means for selecting a desired identification tissue and a separate tissue desired to be separated from the identification tissue from among the number of tissues, wherein the calculation means may comprise:

simulated image constructing means for constructing a simulated image using the plurality of different energy spectra and the X-ray attenuation coefficient of the identification tissue and the separate tissue;

histogram generating means for generating a histogram to present pixel distribution of the identification tissue and the separate tissue; and index calculating means for calculating the index from overlapping degree of the histograms of the identification tissue and the separate tissue. Also, the simulated image constructing means may comprise:

effective energy calculating means for calculating the respective effective energies of the plurality of different energy spectra;

CT value calculating means for calculating a CT value of the identification tissue and the separate tissue using the X-ray attenuation coefficient of the calculated effective energies;

tomographic image noise calculating means for calculating amount of noise on the tomographic image which is calculated based on tube current values; and means for constructing a simulated image based on the CT value and the amount of noise on the tomographic image. Also, the tomographic image noise calculating means may comprise:

means for calculating amount of noise on projection data based on the tube current values; and conversion means for converting the amount of noise on projection data into the amount of noise on image data.

Also, scanning condition determining method of the X-ray CT apparatus related to the present invention comprises:

step (1) for inputting information on an identification tissue of the object to be identified and a separate tissue desired to be separated from the identification tissue on the tomographic image obtained by the X-ray CT apparatus; and step (2) for determining the scanning condition for identifying the identification tissue from the tomographic image. For example, step (2) may select two or more spectra from among the plurality of different energy spectra.

For example, step (2) may select the tube voltages of the plurality of different energy spectra.

For example, the step (2) may include step (3) for calculating the index on accuracy in identifying the identification tissue on the tomographic image reconstructed by obtaining transmitted X-ray data generated by two or more arbitrary selected plurality of energy spectra.

For example, the step (3) may be set so as to calculate the index regarding the combination of the plurality of tube voltages of the plurality of different energy spectra.

For example, the step (2) may be set so as to select the combination of the tube voltages having the index with high accuracy from among the indexes.

For example, the step (2) may include a step for displaying the indexes in the form of a table chart with respect to the combinations of the plurality of tube voltages.

Also, the step (2) may include:

step (4) for storing a plurality of different energy spectra and X-ray attenuation coefficient of a number of tissues of the object; and step (5) for selecting a desired identification tissue and a separate tissue desired to be separated from the identification tissue from among the number of tissues, and the step (3) may include:

step (6) for generating a simulated image using the plurality of different energy spectra and X-ray attenuation coefficient of the identification tissue and the separate tissue;

step (7) for generating a histogram to present pixel distribution of the identification tissue and the separate tissue from the simulated image obtained in step (6); and step (8) for calculating the index from overlapping degree of the histogram of the identification tissue and the separate tissue s.

Also, for example, step (6) may comprise:

step (9) for calculating the respective effective energies of the plurality of different energy spectra;

step (10) for calculating CT value of the identification tissue and the separate tissue using X-ray attenuation coefficient of the calculated effective energy;

step (11) for calculating amount of noise on the tomographic image which is calculated based on tube current values; and step (12) for constructing a simulated image based on the CT value and the amount of noise on the tomographic image.

Also, the step (11) may include:

step (13) for calculating amount of noise on projection data based on the tube current values; and step (14) for converting the amount of noise on projection data into the amount of noise on image data.

Also, the description herein of specific embodiments is not intended to limit the present invention to the particular forms described, and various changes may be made without departing from the scope of the invention. For example, two irradiated X-rays may be selected by the tube voltage. At this time, since there are cases that the irradiated X-ray energy spectra are different even when the voltages are the same, it may be selected by the energy spectra. Also, while identification rate is used as the index regarding accuracy of identification, it may be set so that TPF (True Positive Fraction) in ROC analysis may be acquired and stored in advance as data in the respective scanning conditions for reference.

The invention claimed is:

1. An X-ray CT apparatus comprising:
    a scanner unit rotating one or more X-ray sources for irradiating X-rays having a plurality of different energy spectra to an object to be examined, and detectors disposed facing the X-ray sources for detecting transmitted X-ray data of the object, around the object while irradiating X-rays;
    reconstruction means for acquiring transmitted X-ray data of the object having two or more different energy spectra by the scanner unit, and reconstructing a tomographic image of the object; and
    display means for displaying the reconstructed tomographic image,
    characterized in further comprising:
    input means for inputting the information on an identification tissue of the object to be identified from the tomographic image and a separate tissue to be separated from the identification tissue; and
    scanning condition determining means for determining scanning condition for identifying the identification tissue from the tomographic image.

2. The X-ray CT apparatus according to claim 1, wherein the scanning condition determining means is irradiated X-ray spectrum selecting means which arbitrarily selects two or more energy spectra from the plurality of different energy spectra.

3. The X-ray CT apparatus according to claim 2, wherein the irradiated X-ray spectrum selecting means selects the tube voltage from the plurality of different energy spectra.

4. The X-ray CT apparatus according to claim 3, wherein the scanning condition determining means comprises calculation means for calculating the index related to the accuracy in identifying the identification tissue on the tomographic image reconstructed by acquiring transmitted X-ray data having the arbitrary two or more selected plurality of energy spectra.

5. The X-ray CT apparatus according to claim 4, wherein the calculation means calculates the index with respect to the combination of the plurality of tube voltages which generate the plurality of different energy spectra.

6. The X-ray CT apparatus according to claim 5, wherein the irradiated X-ray spectrum selecting means selects the combination of the tube voltages having the index with high accuracy from among the indexes.

7. The X-ray CT apparatus according to claim 5, wherein the display means displays the indexes in the form of a table chart with respect to the combinations of the plurality of tube voltages.

8. The X-ray CT apparatus according to claim 4, wherein:
    the scanning condition determining means comprises storing means for storing a plurality of different energy spectra and X-ray attenuation coefficient of a number of tissues of the object, and tissue selecting means for selecting a desired identification tissue from among the number of tissues and a separate tissue desired to be separated from the identification tissue; and
    the calculation means comprises simulated image constructing means for generating a simulated image using the plurality of different energy spectra and X-ray attenuation coefficient of the identification tissue and separate tissue, histogram generating means for generating histograms indicating pixel distribution of the identification tissue and the separate tissue, and index calculating means for calculating the index from overlapping degree of the histograms of the identification tissue and the separate tissue.

9. The X-ray CT apparatus according to claim 8, wherein the simulated image constructing means comprises:
    effective energy calculating means for calculating the respective effective energies of the plurality of different energy spectra;
    CT value calculating means for calculating a CT value of the identification tissue and the separate tissue using X-ray attenuation coefficient of the calculated effective energy, tomographic image noise calculating means for calculating amount of noise on the tomographic image calculated based on tube current values, and means for constructing a simulated image based on the CT value and amount of noise on the tomographic image.

10. The X-ray CT apparatus according to claim 9, wherein the tomographic noise calculating means comprises:
- means for calculating amount of noise on projection data based on the tube current values; and
- conversion means for converting the noise of amount on projection data into the amount of noise on image data.

11. A scanning condition determining method in an X-ray CT apparatus comprising:
- (1) a step for inputting information on an identification tissue of an object to be identified and a separate tissue desired to be separated from the identification tissue on a tomographic image obtained by the X-ray CT apparatus; and
- (2) a step for determining the scanning condition for identifying the identification tissue from the tomographic image.

12. The scanning condition determining method in the X-ray CT apparatus according to claim 11, wherein the step (2) is for selecting arbitrary two or more energy spectra from among the plurality of different energy spectra.

13. The scanning condition determining method in the X-ray CT apparatus according to claim 12, wherein the step (2) is for selecting the tube voltage which generates the plurality of different energy spectra.

14. The scanning condition determining method in the X-ray CT apparatus according to claim 13, wherein the step (2) includes:
- (3) a step for calculating an index related to the accuracy in identifying the identification tissue on the tomographic image reconstructed from transmitted X-ray data acquired using arbitrary two or more selected plurality of energy spectra.

15. The scanning condition determining method in the X-ray CT apparatus according to claim 14, wherein the step (3) calculates the index with respect to the combination of the plurality of tube voltages of the plurality of different energy spectra.

16. The scanning condition determining method in the X-ray CT apparatus according to claim 15, wherein the step (2) selects the combination of the tube voltages having the index with high accuracy from among the indexes.

17. The scanning condition determining method in the X-ray CT apparatus according to claim 15, wherein the step (2) includes a step for displaying the indexes in the form of a table chart with respect to the combinations of the plurality of tube voltages.

18. The scanning condition determining method according to claim 14, wherein the step (2) comprises:
- (4) a step for storing the plurality of different energy spectra and X-ray attenuation coefficient of the number of tissues of the object; and
- (5) a step for selecting the desired identification tissue from among the number of tissues and a separate tissues desired to be separated from the identification tissue, and the step (3) includes:
- (6) a step for constructing a simulated image using the plurality of different energy spectra and X-ray attenuation coefficients of the identification tissue and the separate tissue;
- (7) a step for generating histograms indicating the pixel distribution of the identification tissue and the separate tissue from the simulated image obtained in the step (6); and
- (8) a step for calculating the index from the overlapping degree of the histograms of the identification tissue and the separate tissue.

19. The scanning condition determining method according to claim 18, wherein the step (6) comprises:
- (9) a step for calculating the respective effective energies of the plurality of different energy spectra;
- (10) a step for calculating a CT value of the identification tissue and the separate tissue using X-ray attenuation coefficient of the calculated effective energies;
- (11) a step for calculating amount of noise on the tomographic image calculated based on current values; and
- (12) a step for constructing a simulated image based on tomographic image noise calculating means, the CT values and amount of noise on the tomographic image.

20. The scanning condition determining method according to claim 19, wherein the step (11) includes:
- (13) a step for calculating amount of noise on projection data based on the tube current values; and
- (14) a step for converting the amount of noise on projection data into amount of noise on image data.

* * * * *